(12) United States Patent
Li et al.

(10) Patent No.: US 12,310,706 B2
(45) Date of Patent: May 27, 2025

(54) WEARABLE DEVICE

(71) Applicant: Huawei Technologies Co., Ltd., Shenzhen (CN)

(72) Inventors: Kelin Li, Xi'an (CN); Zhi Guo, Xi'an (CN); Yongtao Cui, Dongguan (CN); Rongguang Yang, Dongguan (CN); Yi Xi, Dongguan (CN)

(73) Assignee: HUAWEI TECHNOLGOIES CO., LTD., Shenzhen (CN)

( * ) Notice: Subject to any disclaimer, the term of this patent is extended or adjusted under 35 U.S.C. 154(b) by 29 days.

(21) Appl. No.: 18/040,553

(22) PCT Filed: Aug. 5, 2021

(86) PCT No.: PCT/CN2021/110725
§ 371 (c)(1),
(2) Date: Feb. 3, 2023

(87) PCT Pub. No.: WO2022/028502
PCT Pub. Date: Feb. 10, 2022

(65) Prior Publication Data
US 2023/0293033 A1    Sep. 21, 2023

(30) Foreign Application Priority Data
Aug. 6, 2020 (CN) .......................... 202010782990.4

(51) Int. Cl.
*A61B 5/024* (2006.01)
*A61B 5/256* (2021.01)
*A61B 5/282* (2021.01)

(52) U.S. Cl.
CPC ...... *A61B 5/02438* (2013.01); *A61B 5/02416* (2013.01); *A61B 5/256* (2021.01); *A61B 5/282* (2021.01)

(58) Field of Classification Search
CPC . A61B 5/02438; A61B 5/02416; A61B 5/256; A61B 5/282; A61B 5/681;
(Continued)

(56) References Cited

U.S. PATENT DOCUMENTS

| | | | |
|---|---|---|---|
| 10,729,347 B1* | 8/2020 | Schleicher | A61B 5/332 |
| 2009/0294765 A1* | 12/2009 | Tanaka | H01L 21/28194 |
| | | | 257/E29.296 |

(Continued)

FOREIGN PATENT DOCUMENTS

| | | |
|---|---|---|
| CN | 106293258 A | 1/2017 |
| CN | 106388809 A | 2/2017 |

(Continued)

*Primary Examiner* — Baisakhi Roy
*Assistant Examiner* — Kaitlyn E Sebastian
(74) *Attorney, Agent, or Firm* — Conley Rose, P.C.

(57) ABSTRACT

A wearable device includes a screen, a first electrode, a second electrode, and a circuit board. The screen and the second electrode are mounted on a housing. The first electrode is coupled to the screen and does not shield a display region of the screen, and the first electrode and the second electrode are electrically coupled by the circuit board. The first electrode has a first surface, the second electrode has a second surface, and the first surface and the second surface are configured to contact a human body of a wearer.

20 Claims, 4 Drawing Sheets

(58) Field of Classification Search
CPC ....... A61B 5/6831; A61B 5/339; A61B 5/332; A61B 5/02
See application file for complete search history.

(56) References Cited

U.S. PATENT DOCUMENTS

| | | |
|---|---|---|
| 2010/0076331 A1 | 3/2010 | Chan et al. |
| 2013/0281814 A1* | 10/2013 | Tilt ........................ A61B 5/282 |
| | | 600/382 |
| 2016/0338598 A1 | 11/2016 | Kegasawa |
| 2019/0072912 A1* | 3/2019 | Pandya .................. A61B 5/332 |
| 2020/0233381 A1* | 7/2020 | Yang .................. A61B 5/02055 |

FOREIGN PATENT DOCUMENTS

| | | | | |
|---|---|---|---|---|
| CN | 107865653 A | * | 4/2018 | ........... A61B 5/0537 |
| CN | 110244546 A | | 9/2019 | |
| CN | 111199999 A | | 5/2020 | |
| KR | 20070080330 A | * | 8/2007 | |
| WO | 2018129847 A1 | | 7/2018 | |

* cited by examiner

WEARABLE DEVICE

CROSS-REFERENCE TO RELATED APPLICATIONS

This is a U.S. National Stage of International Patent Application No. PCT/CN2021/110725 filed on Aug. 5, 2021, which claims priority to Chinese Patent application No. 202010782990.4 filed on Aug. 6, 2020. Both of the aforementioned applications are hereby incorporated by reference in their entireties.

TECHNICAL FIELD

This application relates to the field of intelligent device technologies, and in particular, to a wearable device.

BACKGROUND

With improvement of living standards, people pay more attention to health conditions. To facilitate detection of health conditions, people usually wear wearable devices such as smart bands, so as to detect data such as an electrocardiogram and a heart rate. The smart band includes a first electrode and a second electrode. The second electrode is located on a side of the smart band of the wearable device away from a screen. The first electrode may be located on the screen or a side surface of the smart band. For example, when a user wears the smart band on the left arm, the left arm is in contact with the second electrode, and when in use, the right arm is in contact with the first electrode, so as to form a complete loop. However, it is inconvenient for the user to obtain detected results through the screen because the first electrode usually occupies a display region of the screen. When the first electrode is located on the side surface of the smart band, the right arm is contact with the first electrode, which is likely to push the smart hand to displace relative to the left arm. Consequently, poor contact between the second electrode and the left arm is caused.

SUMMARY

This application provides a wearable device, so as to solve a problem that an electrode of the wearable device occupies a display region of a screen and is prone to poor contact with a human body.

Embodiments of this application provide a wearable device, having a screen, a first electrode, a second electrode, and a circuit board.

The first electrode is connected to the screen and does not shield a display region of the screen, and the second electrode is mounted on a housing of the wearable device. The first electrode and the second electrode are electrically connected by using the circuit board.

In a thickness direction of the wearable device, the first electrode has a first surface, the second electrode has a second surface, and the first surface and the second surface are used to contact a human body.

Such a design can reduce impact of the first electrode on the display region of the screen. The first surface and the second surface used to contact the human body are disposed in the thickness direction of the wearable device, so that the wearable device can be clamped when a user uses the wearable device. Therefore, a possibility that the wearable device is displaced relative to the user can be reduced, and stability of contact between the human body and the first electrode and the second electrode can be improved.

In a possible implementation, a groove is disposed in the screen, the groove is disposed on a side of the screen facing the user, and the first electrode is disposed along the groove.

Such a design can facilitate positioning of the first electrode during mounting, thereby improving accuracy of a mounting position of the first electrode and reducing a possibility that the first electrode affects the display region of the screen.

In a possible implementation, the first electrode is made of a nanometal.

It is difficult to observe the nanometal with naked eyes because a width of the nanometal is relatively small and is usually calculated in a unit of nanometer, and therefore, the possibility that the first electrode affects the display region of the screen can be reduced.

In a possible implementation, a plurality of grooves are disposed in the screen, and the grooves are distributed in a form of a grid. A nanometal is disposed in each groove, and adjacent nanometals are connected to each other to form the first electrode.

The first electrode can be distributed more properly by being disposed in the grooves distributed in the form of a grid, so that a distribution area of the first electrode can be increased, further facilitating contact between the first electrode and the user.

In a possible implementation, the screen has a third surface away from the circuit board, and the groove is disposed in the third surface; and a conductive protective layer is disposed on the third surface, and the conductive protective layer at least covers a region in which the first electrode is located, and is electrically connected to the first electrode.

The conductive protective layer is disposed on the third surface to protect the first electrode. An area of the conductive protective layer may be larger than that of the first surface, and the conductive protective layer can be electrically connected to the first electrode, further facilitating contact between the user and the first surface; and is electrically connected to the first electrode.

In a possible implementation, the first electrode has a first main body part, a second main body part, and a connecting section. The first main body part is disposed in the groove, and the second main body part is disposed on a side of the screen away from the third surface, and is configured to electrically connect to the circuit board. The first main body part and the second main body part are electrically connected by using the connecting section.

In this manner, connection between the first electrode and the circuit board is further facilitated. Compared with changing of a structure of the circuit board, the solution provided in this embodiment of this application is simpler and easier to operate.

In a possible implementation, the housing is connected to the screen, and at least a portion of the housing is made of a conductive ceramic that is configured to form the first electrode.

The conductive ceramic is disposed on the housing to form the first electrode, so as to further reduce the impact of the first electrode on the display region of the screen. In addition, compared with a metal electrode, the conductive ceramic can effectively reduce a possibility of occurrence of an electro-static discharge phenomenon, and improve accuracy of a detection result.

In a possible implementation, the first electrode is in a form of a ring, and is sleeved to the screen.

The housing may be entirely made of the conductive ceramic, so that the screen can be mounted on the housing more conveniently, improving integrity of the housing. In addition, the conductive ceramic is sleeved to the screen in the form of a ring, so that the user can be in contact with the first electrode by being in contact with any position along an edge of the screen.

In a possible implementation, the wearable device further includes an elastic part through which the first electrode is electrically connected to the circuit board.

The elastic part is disposed between the first electrode and the circuit board to improve stability of electrical connection between the first electrode and the circuit board.

In a possible implementation, the housing has a fourth surface away from the screen, and the second electrode is disposed on the fourth surface.

With such a design, the first electrode and the second electrode can be disposed oppositely, so that the user can clamp the wearable device more conveniently.

In a possible implementation, the housing includes a bottom housing that is located on a side of the wearable device facing the human body; and the fourth surface is located on the bottom housing.

Such a design can facilitate contact between the second electrode and a wearer when the wearable device is worn, and improve stability of contact between the second electrode and the wearer.

In a possible implementation, the wearable device includes a plurality of second electrodes.

The plurality of second electrodes are disposed, so that the second electrodes can be distributed more uniformly, facilitating contact between the second electrodes and the wearer and improving stability of contact between the second electrode and the wearer In a possible implementation, the wearable device further includes an electrocardiogram module, and the electrocardiogram module is electrically connected to the first electrode and the second electrode by using the circuit board.

By disposing the electrocardiogram module, the wearable device can detect a heart rate, an electrocardiogram, and the like of the user, so that the user can intuitively learn of a health condition of the user.

In a possible implementation, the wearable device further includes a photoplethysmography module that is mounted on the housing and configured to detect a heart rate of the human body.

The photoplethysmography module is disposed to detect data such as the heart rate of the human body, so that the wearer can learn of the health condition of the wearer more conveniently.

The embodiments of this application provide a wearable device that may be a smart band or the like. Specifically, the wearable device includes a screen, a first electrode, a second electrode, and a circuit board. The screen and the second electrode are mounted on a housing, the first electrode is connected to the screen and does not shield a display region of the screen, and the first electrode and the second electrode are electrically connected by using the circuit board. In a thickness direction of the wearable device, the first electrode has a first surface, the second electrode has a second surface, and the first surface and the second surface are used to contact a human body. Such a design can effectively reduce impact of the first electrode on the display region of the screen. In addition, the wearable device can be clamped when a user is in contact with the first surface and the second surface, so that a possibility that the wearable device is displaced relative to the user can be reduced.

It should be understood that the foregoing general description and the following detailed description are merely examples; and cannot limit this application.

REFERENCE NUMERALS 1. housing;
11. fourth surface;
12. bottom housing;
2. screen;
21. groove;
22. third surface;
3. first electrode;
31. first surface;
32. connecting section;
33. first main body part;
34. second main body part;
4. second electrode;
41. second surface;
5. circuit board; and
6. elastic part, The accompanying drawings herein are incorporated into the specification and form a part of the specification, show embodiments conforming to this application, and are used together with the specification to explain a principle of this application.

DESCRIPTION OF EMBODIMENTS

To better understand the technical solutions of this application, the following describes embodiments of this application in detail with reference to the accompanying drawings.

It should be clear that the described embodiments are merely some rather than all of embodiments of this application. All other embodiments obtained by a person of ordinary skill in the art based on embodiments of this application without creative efforts shall fall within the protection scope of this application.

The terms used in embodiments of this application are merely for the purpose of illustrating specific embodiments, and are not intended to limit this application. The terms "a" and "the" of singular forms used in embodiments and the appended claims of this application are also intended to include plural forms, unless otherwise specified in the context clearly.

It should be understood that the term "and/or" in this specification describes only an association relationship for describing associated objects and represents that three relationships may exist. For example. A and/or B may represent the following three cases: Only A exists, both A and B exist, and only B exists. In addition, the character "/" in this specification generally indicates an "or" relationship between the associated objects.

It should be noted that, position words such as "above", "below", "left", and "right" described in embodiments of this application are described from angles shown in the accompanying drawings, and should not be construed as a limitation on embodiments of this application. Moreover, in the context, it should be further understood that, when it is mentioned that one element is connected "above" or "below" another element, one element can not only be directly connected "above" or "below" the another element, but also be indirectly connected "above" or "below" the another element by using an intermediate element.

With the improvement of living standards, people pay more attention to their health conditions. To facilitate detection of their health conditions, people usually wear electronic devices such as smart bands, so as to detect health data of the body. Being taken as an example, a smart band includes a first electrode and a second electrode. The first electrode and the second electrode are parts made of materials with conductivity and are used to contact a human body. The first electrode and the second electrode are in contact with the human body and conduct bioelectricity, generated by the human body. The first electrode and the second electrode are usually made of metal materials. The second electrode is usually disposed on a back side of the smart band: a side of the smart band away from a screen. For example, the smart band is worn on the left arm. The left arm is in contact with the second electrode when a user wears the smart band. When data such as a heart rate and an electrocardiogram needs to be detected, the user may use the right hand to touch the first electrode, so that the double arms, the torso, and the smart band form a closed loop passing through a position of the heart. An electrocardiogram module inside the smart band detects bioelectricity of the human body of the user by using the first electrode and the second electrode, so that an electrocardiogram can be generated. In addition, a detection result is displayed on the screen of the smart band, so that the user can intuitively learn of a. health condition of the user.

Generally, the first electrode is disposed on the screen or a side surface of the smart band. When the first electrode is disposed on the screen, disposing the first electrode on the screen occupies a space of the screen because the first electrode is usually made of a metal sheet, thereby reducing an area of a display region of the screen. This is inconvenient for the user to obtain the detection result. In order not to occupy the display region of the screen, the first electrode may alternatively be disposed on the side surface of the smart band, for example, at a position such as a side button. However, in actual use, the user usually applies an acting force on the first electrode, so that the right hand can be in good contact with the first electrode. Because the first electrode is disposed on the side surface of the smart band, when the user applies the acting force on the first electrode, the smart band is pushed to move relative to the left arm. Because the smart band is displaced relative to the left arm, poor contact between the second electrode and the left arm is easily caused, thus affecting accuracy of the detection result.

In view of this, an embodiment of this application provides a wearable device, so as to solve a problem in the conventional technology that an electrode occupies a display region of a screen and is prone to poor contact with a human body.

As shown in FIG. 1 to FIG. 4, an embodiment of this application provides a wearable device, having a screen 2, a first electrode 3, a second electrode 4, and a circuit board 5. The first electrode 3 is connected to the screen 2 and does not shield a display region of the screen 2. For example, the first electrode 3 may be in a form of a grid and is disposed on a surface of a side of the screen 2 facing a user. A portion of the screen covered by the first electrode 3 in the form of a grid and a portion in a mesh form the display region; or the first electrode 3 is disposed in a circumferential direction of the screen 2 to avoid the surface of the side of the screen 2 facing the user, where the surface of the side of the screen 2 facing the user is the display region. The first electrode 3 and the second electrode 4 are electrically connected by using the circuit hoard 5. Specifically, in a thickness direction of the wearable device, the first electrode 3 has a first surface 31 used to contact a human body, and the second electrode 4 has a second surface 41 also used to contact the human body. In a possible implementation, the first surface 31 may be in contact with the right hand of the user, and the second surface 41 may be in contact with the left hand of the user, so that the wearable device, the double arms, and the torso of the user form a closed loop, and the wearable device can detect bioelectricity generated by the user so as to obtain electrocardiogram data of the user.

The wearable device provided in the embodiment of this application can reduce impact of the first electrode 3 on the display region of the screen 2. In the thickness direction of the wearable device, the first electrode 3 has the first surface 31, and the second electrode 4 has the second surface 41. By disposing the first electrode 3 and the second electrode 4 oppositely, the user can clamp the wearable device, for example, between the left hand and the right hand, while applying an acting force on the first surface 31 and the second surface 41, so that a possibility that the wearable device is displaced relative to the human body can be reduced. The first electrode 3 and the second electrode 4 can be in good contact with the human body, so that a detection result can be more accurate.

To facilitate the description of the technical solutions provided in the embodiments of this application, a smart band is taken as an example for description in the specification of the embodiments of this application. It should be noted herein that the wearable device provided in the embodiments of this application includes but is not limited to a smart band. Other devices such as a watch, a mobile phone, and a tablet computer may adopt the technical solutions provided in the embodiments of this application, adopt the same principle, and achieve the same technical effect, which are not detailed herein.

Figure 1:
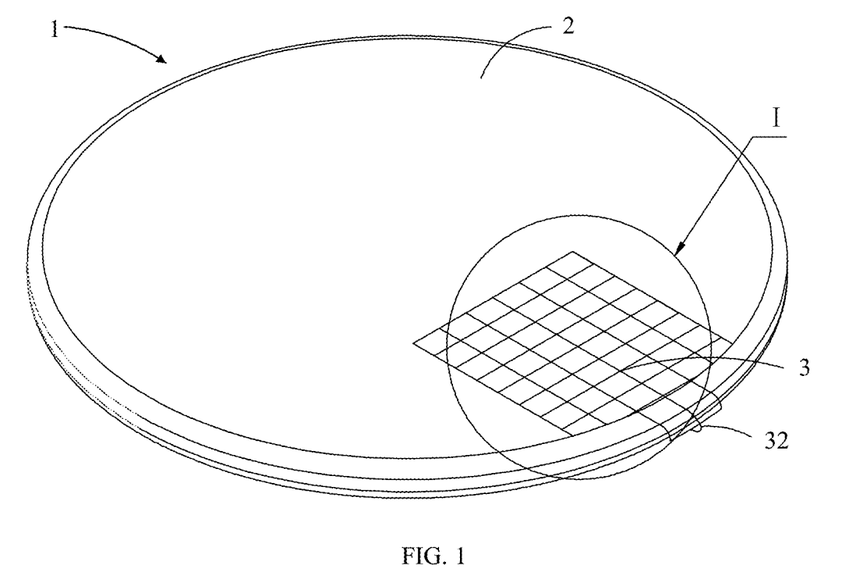
FIG. 1 is a schematic diagram of a structure of a first embodiment of a wearable device according to an embodiment of this application.
Figure 2:
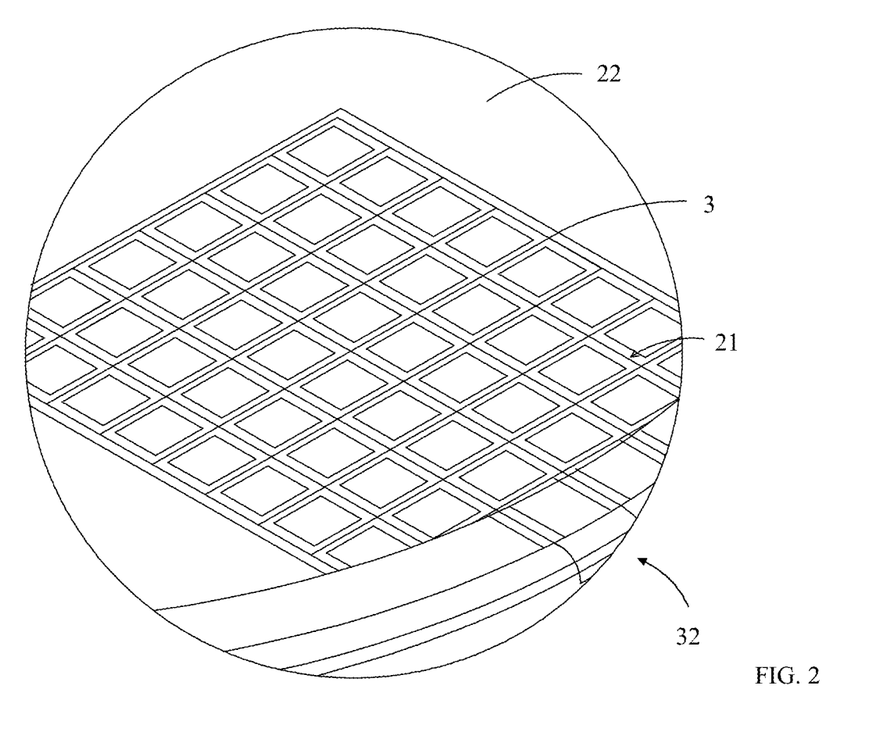
FIG. 2 is a partially enlarged view of a position I in FIG. 1.

As shown in FIG. 2, in a possible implementation, a groove 21 is disposed in the screen 2 of the smart band, and the groove 21 is located on a side of the screen 2 facing the user. Specifically, the groove 21 may be disposed on an edge of the screen 2, and the first electrode 3 is disposed along the groove 21.

According to the technical solution provided in this embodiment of this application, by disposing the groove 21 in the screen 2 and disposing the first electrode 3 in the groove 21, positioning of the first electrode 3 can be facilitated during processing to improve position accuracy of the first electrode 3, so that a possibility that the first electrode 3 shields the display region of the screen 2 can be reduced. Disposing the groove 21 at an edge position of the screen 2 can further reduce the impact on the display region of the screen 2.

In a possible implementation, the first electrode 3 is made of a nanometal. Specifically, the first electrode 3 may be made of nano silver paste. It is difficult to observe the nano silver paste with naked eyes because a width of the nano silver paste is relatively small, and is usually only a few nanometers, Therefore, the impact of the first electrode 3 on the display region of the screen 2 can be effectively reduced.

As shown in FIG. 2, in a possible implementation, a plurality of grooves 21 are disposed in the screen 2, and the grooves 21 are distributed in a form of a grid. A first electrode 3 is correspondingly disposed in each groove 21.

In this way, a distribution area of the first electrode 3 can be increased without increasing the width of the nanometal, thereby facilitating contact between the first electrode 3 and the user, and improving stability of contact between the first electrode 3 and the user.

In a possible implementation, because the impact of the first electrode 3 on the display region of the screen 2 is relatively small, an indication identifier may be displayed in a region of the screen 2 corresponding to the first electrode 3. When a health condition of the user needs to be detected by using the smart band, the screen 2 of the smart band displays a corresponding identifier to remind the user of a position of the first electrode 3. This facilitates use by the user and better meets an actual use requirement.

In a possible implementation, the screen 2 has a third surface 22 that is located on a side of the screen 2 away from the circuit board 5, and the groove 21 is disposed in the third surface 22, so as to facilitate contact with the user. Specifically, a conductive protective layer may further be disposed on the third surface 22, covers at least a region in which the first electrode 3 is located, and is electrically connected to the first electrode 3.

With such a design, the first electrode 3 can be protected to reduce a possibility of causing damage to the first electrode 3. In addition, a set area of the conductive protective layer may be greater than that of the first surface 31. Because the conductive protective layer is electrically connected to the first electrode 3, the user can be in contact with the first surface 31 of the first electrode 3 by being in contact with the conductive protective layer. Therefore, stability of contact between the user and the first electrode 3 can be effectively improved, better meeting an actual use requirement.

In a possible implementation, the conductive protective layer is a transparent conductive protective layer, and is disposed on the third surface 22 by spraying. With such a design, shielding of the conductive protective layer on the screen 2 can be effectively reduced, thereby reducing the impact on the display region of the screen 2.

Figure 3:
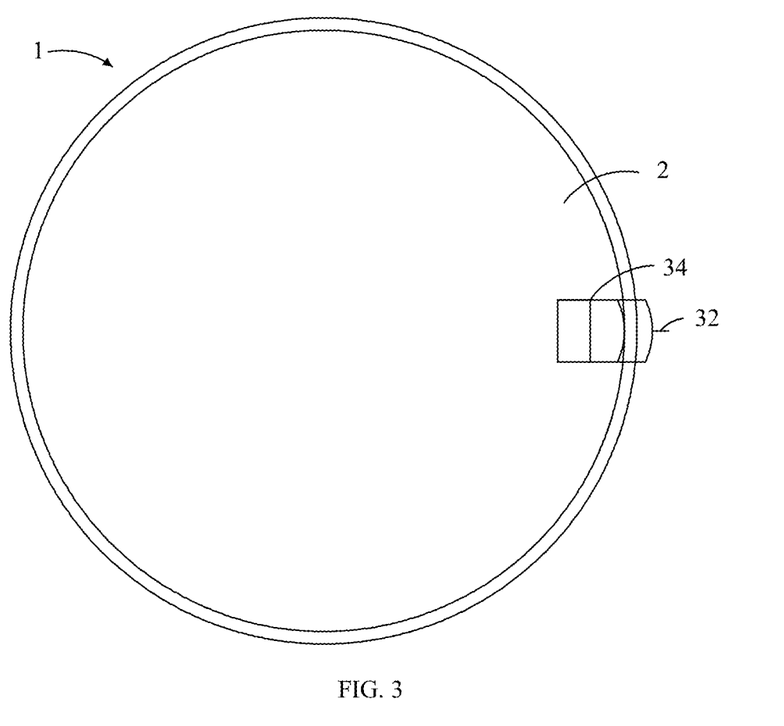
FIG. 3 is a bottom view of a screen of a wearable device according to an embodiment of this application.
Figure 4:
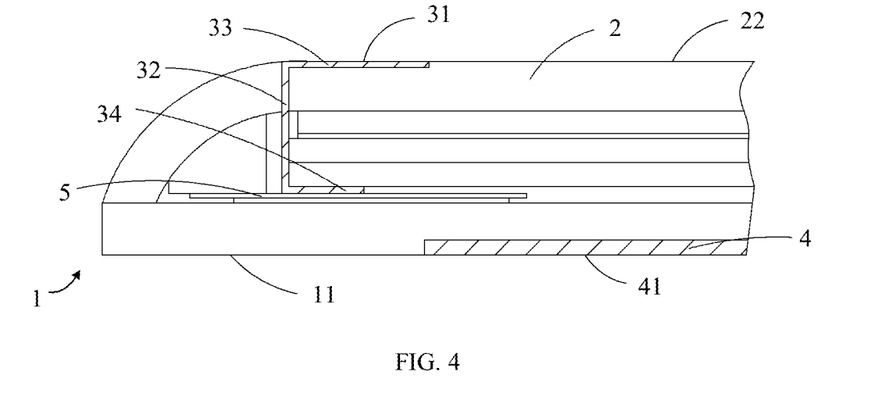
FIG. 4 is a partial cross-sectional view of a first embodiment of a wearable device according to an embodiment of this application.

As shown in FIG. 3 and FIG. 4, in a possible implementation, the first electrode 3 has a first main body part 33, a second main body part 34, and a connecting section 32. The first main body part 33 is disposed in the groove 21, and the second main body part 34 is disposed on a side of the screen 2 away from the third surface 22, that is, the first main body part 33 and the second main body part 34 are oppositely disposed. The first surface 31 is located on the first main body part 33, and the second main body part 34 is configured to electrically connect to the circuit board 5; and the first main body part 33 and the second main body part 34 are electrically connected by using the connecting section 32.

With such a design, electrical connection between the first electrode 3 and the circuit board 5 is further facilitated. Compared with a solution of facilitating electrical connection between the first electrode 3 and the circuit board 5 by changing a shape of the circuit board 5, the solution provided in the embodiment of this application is more convenient during processing, easier to operate, and better meets an actual use requirement.

Figure 5:
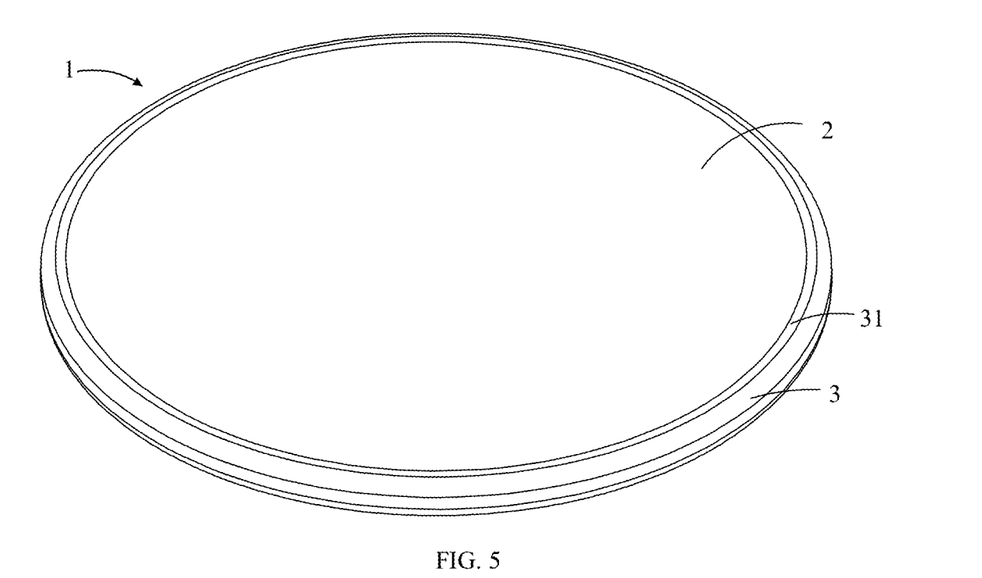
FIG. 5 is a schematic diagram of a structure of a second embodiment of a wearable device according to an embodiment of this application.

As shown in FIG. 5, in a possible implementation, a housing 1 is connected to the screen 2. Specifically, the housing 1 may be disposed along the edge of the screen, and at least a portion of the housing 1 is made of a conductive ceramic that may be used to form the first electrode 3.

According to the wearable device provided in the embodiment of this application, the conductive ceramic is disposed on the housing 1 to form the first electrode 3, so that a space occupied by the first electrode 3 on the screen 2 can be effectively reduced, and the health condition of the user can be obtained by the user more conveniently by using the screen 2.

Generally, the electrode of the smart band is made of a metal material, and an electro-static discharge (Electro-Static discharge, ESD) phenomenon is easy to occur. Because a working principle of the smart band is to detect various health indicators of the human body by detecting bioelectricity generated by the human body of the user, when static electricity is generated by the metal electrode, a detection result of the smart band is easily affected, and accuracy of the detection result is reduced. However, according to the solution provided in the embodiment of this application, the first electrode 3 is made of the conductive ceramic, so that a possibility that the electro-static discharge phenomenon occurs can be effectively reduced, and impact of static electricity on the detection result of the smart band can be reduced, improving accuracy of the detection result.

As shown in FIG. 5, in a possible implementation, the first electrode 3 is in a form of a ring, and is sleeved to the screen 2. That is, the housing 1 of the smart hand may be manufactured by using a conductive ceramic.

With such a design, a connection step between the conductive ceramic and the housing 1 can be effectively reduced, integrity of the housing 1 is improved, the process is simplified, and production efficiency is improved. In addition, with such a design, the area of the first surface 31 of the first electrode 3 can be increased, and contact between the user and the first electrode 3 is further facilitated. Because the conductive ceramic is sleeved to the screen 2 in the form of a ring, the user can be in contact with the first electrode 3 by being in contact with any position along the edge of the screen 2. When in use, the position of the first electrode 3 does not need to be searched for based on an identifier. This facilitates use and better meets an actual use requirement.

Figure 6:
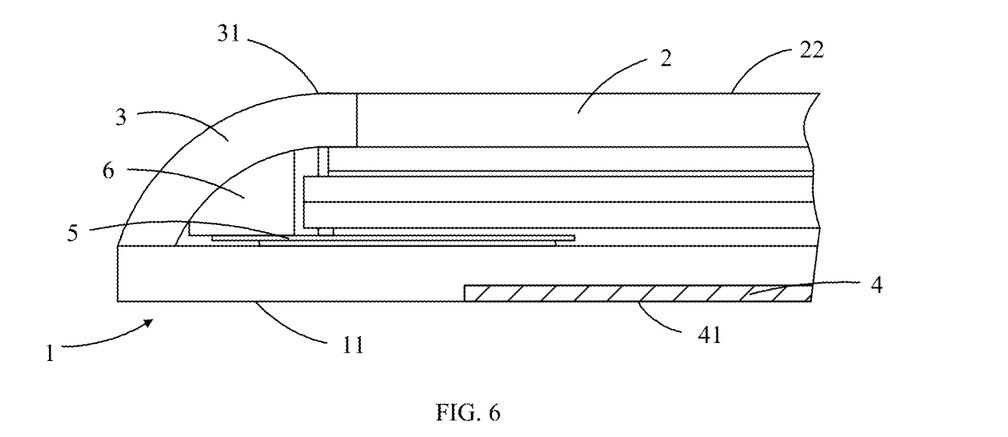
FIG. 6 is a partial cross-sectional view of a second embodiment of a wearable device according to an embodiment of this application.

As shown in FIG. 6, in a possible implementation, the wearable device further includes an elastic part 6 through which the circuit hoard 5 is electrically connected to the first electrode 3.

Specifically, the elastic part 6 may be a conductive elastic sheet, conductive foam, or the like. In a process of assembling the smart band, the elastic part 6 is located between the first electrode 3 and the circuit board 5, and when the housing 1 is made of the conductive ceramic, the elastic part 6 may be disposed between the housing 1 and the circuit board 5. When assembled, the first electrode 3 and the circuit board 5 abut against the elastic part 6, so that the elastic part 6 is elastically deformed. The elastic part 6 has a movement trend to recover the deformation, and therefore, the elastic part 6 abuts against the first electrode 3 and the circuit board 5 under an action of a restoring force to improve stability of electrical connection.

As shown in FIG. 6, in a possible implementation, the housing 1 has a fourth surface 11 that is located on a side of the housing 1 away from the screen 2, and the second electrode 4 is disposed on the fourth surface 11.

Such a design further facilitates contact between the second electrode 4 and the user. When the user wears the smart band, the fourth surface 11 is located on a side of the smart band facing the user's arm. The smart band is worn on the user's arm, and therefore, the second electrode 4 can be in contact with the user's arm.

In a possible implementation, the fourth surface 11 may have a plurality of second electrodes 4, and a contact area between the second electrodes 4 and the user can be increased by disposing the plurality of the second electrodes 4, so that contact between the second electrodes 4 and the user is further facilitated, stability of contact between the second electrodes 4 and the user is improved, and accuracy of the detection result is improved.

In a possible implementation, the wearable device further includes an electrocardiogram module, and the electrocardiogram module is electrically connected to the first electrode 3 and the second electrode 4 by using the circuit board 5.

The electrocardiogram module is disposed, so that the smart band can detect a cardiac function of the user.

A specific electrocardiogram module may include an electrocardiography (Electrocardiography, ECG) module, a photoplethysmogram (Photoplethysmogram, PPG) module, and the like. An electrocardiogram of the user may be generated by using the ECG module, and the PPG module can detect the heart rate of the user. A detection result of the electrocardiogram module may be displayed by using the screen 2, so that the user can more intuitively learn of the health condition of the user; and when a health problem occurs, the user can detect the problem in time and take countermeasures.

Figure 7:
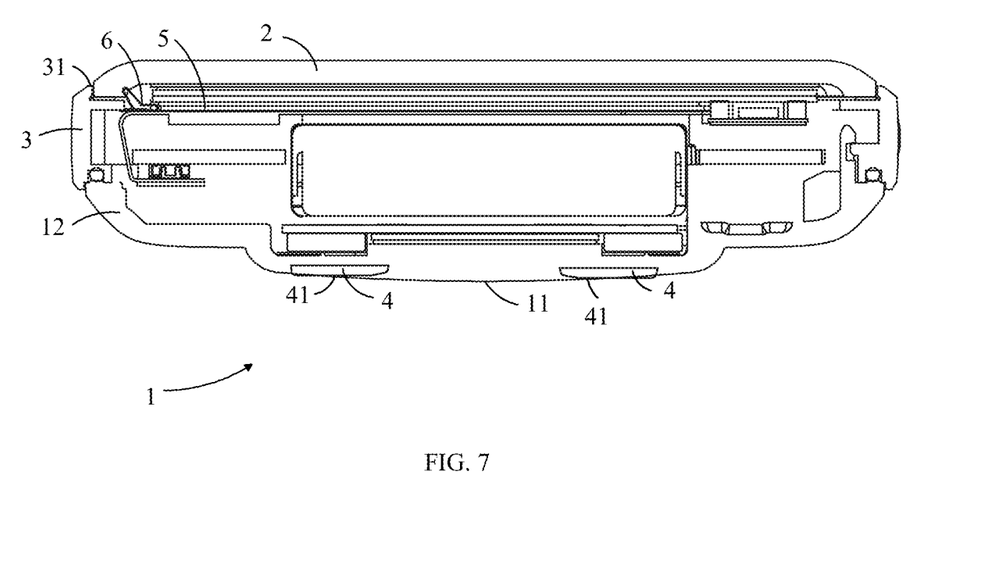
FIG. 7 is a cross-sectional view of a wearable device according to an embodiment of this application.

As shown in FIG. 7, in a possible implementation, the wearable device includes a first electrode 3 made of a conductive ceramic. The first electrode 3 may be sleeved on an outer side of the screen 2 in a form of a ring, the housing 1 has a bottom housing 12, and the fourth surface 11 is located on a side of the bottom housing 12 facing the wearer. Two second electrodes 4 may be disposed on the fourth surface 11. The two second electrodes 4 are disposed, so that the second electrodes 4 can be more uniformly distributed on the fourth surface 11, facilitating contact between the second electrodes 4 and the wearer, and improving stability of contact with the wearer. The wearable device is further provided with an elastic part 6 that may be a conductive spring plate. The first electrode 3 is electrically connected to the circuit board 5 by using the conductive spring plate. Such a design can improve stability of electrical connection between the first electrode 3 and the circuit board 5. The second electrode 4 is also electrically connected to the circuit board 5. When the wearer releases the first surface 31 of the first electrode 3 and the second surface 41 of the second electrode 4 simultaneously, the first electrode 3, the second electrode 4, the circuit board 5, and the human body can form a closed loop to conduct bioelectricity of the human body. The ECG module (not shown in the figure) located in the circuit board 5 may generate an electrocardiogram of the wearer based on the bioelectricity of the human body, so that the wearer can conveniently learn of the health condition of the wearer.

The embodiment of this application provides a wearable device that may be a smart band or the like, Specifically, the wearable device includes a screen 2, a first electrode 3, a second electrode 4, and a circuit board 5. The screen 2 and the second electrode 4 are mounted on a housing 1, the first electrode 3 is connected to the screen 2 and does not shield a display region of the screen 2, and the first electrode 3 and the second electrode 4 are connected by using the circuit board 5. In a thickness direction of the wearable device, the first electrode 3 has a first surface 31, the second electrode 4 has a second surface 41, and the first surface 31 and the second surface 41 are used to contact a human body. Such a design can effectively reduce impact of the first electrode 3 on the display region of the screen 2. In addition, the wearable device can be clamped when a user is in contact with the first surface 31 and the second surface 41, so that a possibility that the wearable device is displaced relative to the user can be reduced, and stability of contact between the human body and the wearable device can be improved.

The foregoing descriptions are merely preferred embodiments of this application, but are not intended to limit this application. For a person skilled in the art, various changes and variations may be made in this application. Any modification, equivalent replacement, or improvement made without departing from the spirit and principle of this application should fall within the protection scope of this application.

What is claimed is:

1. A wearable device comprising:
 a housing;
 a circuit board disposed within the housing;
 a screen comprising:
  a display region;
  a connecting section; and
  a groove disposed on the connecting section and on a portion of the display region;
 a first electrode disposed in the groove and coupled to the screen, wherein the first electrode comprises a first surface; and
 a second electrode mounted on the housing, wherein the second electrode comprises a second surface,
 wherein the first electrode and the second electrode are electrically coupled by the circuit board, and
 wherein the first surface and the second surface are configured to contact a human body of a wearer.

2. The wearable device of claim 1, wherein the first electrode comprises nanometal.

3. The wearable device of claim 2, further comprising a plurality of grooves disposed in the screen, wherein the grooves are distributed in a form of a grid, wherein a nanometal is disposed in each of the grooves, and wherein adjacent nanometals are coupled to each other to define the first electrode.

4. The wearable device of claim 1, further comprising a conductive protective layer disposed on a region of the screen in which the first electrode is located and that is electrically coupled to the first electrode.

5. The wearable device of claim 4, wherein the first electrode further comprises:
 a first main body part disposed in the groove;
 a second main body part and configured to electrically couple to the circuit board; and
 a connecting section coupled to the first main body part and the second main body part to electrically couple the first main body part and the second main body part.

6. The wearable device of claim 1, wherein the housing is coupled to the screen, and wherein the first electrode is defined by a portion of the housing comprising conductive ceramic.

7. The wearable device of claim 6, wherein the first electrode comprises a ring around a circumference of the screen.

8. The wearable device of claim 6, further comprising an elastic part through which the first electrode is electrically coupled to the circuit board.

9. The wearable device of claim 1, wherein the housing comprises a second surface facing away from the screen, and wherein the second electrode is disposed on the second surface.

10. The wearable device of claim 9, wherein the housing comprises a bottom housing configured to contact a wearer, and wherein the second surface is on the bottom housing.

11. The wearable device of claim 9, further comprising a plurality of second electrodes.

12. The wearable device of claim 1, further comprising an electrocardiogram module electrically coupled to the first electrode and the second electrode by the circuit board.

13. The wearable device of claim 1, further comprising a photoplethysmography module mounted on the housing and configured to detect a heart rate of the human body.

14. The wearable device of claim 1, wherein the first electrode comprises a conductive ceramic disposed on the housing.

15. The wearable device of claim 1, wherein the housing comprises conductive ceramic.

16. The wearable device of claim 1, wherein the wearable device is a smart band.

17. The wearable device of claim 1, wherein the screen further comprises an edge, and wherein the groove is further disposed on the edge.

18. The wearable device of claim 2, wherein the nano-metal comprises a nano silver paste.

19. The wearable device of claim 4, wherein the conductive protective layer is a transparent conductive protective layer and is disposed on the third surface using a manner of spraying.

20. The wearable device of claim 1, wherein the housing consists of conductive ceramic sleeved to the screen in the form of a ring.

* * * * *